United States Patent
Miwa et al.

(10) Patent No.: US 8,046,055 B2
(45) Date of Patent: Oct. 25, 2011

(54) LYMPH NODE DETECTOR

(75) Inventors: Mitsuharu Miwa, Hamamatsu (JP); Takahiro Shikayama, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 385 days.

(21) Appl. No.: 11/629,471

(22) PCT Filed: May 25, 2005

(86) PCT No.: PCT/JP2005/009551
§ 371 (c)(1), (2), (4) Date: Dec. 14, 2006

(87) PCT Pub. No.: WO2006/003762
PCT Pub. Date: Jan. 12, 2006

(65) Prior Publication Data
US 2008/0097198 A1   Apr. 24, 2008

(30) Foreign Application Priority Data
Jun. 30, 2004  (JP) .............................. P2004-194691

(51) Int. Cl.
*A61B 6/00* (2006.01)

(52) U.S. Cl. ........ 600/431; 600/473; 600/476; 600/478; 600/472; 356/73; 356/317; 356/318

(58) Field of Classification Search .................. 600/427, 600/428, 431, 475, 476, 478, 479; 356/73, 356/317–318, 417
See application file for complete search history.

(56) References Cited

U.S. PATENT DOCUMENTS

| | | | |
|---|---|---|---|
| 4,821,117 A | 4/1989 | Sekiguchi | |
| 5,111,821 A * | 5/1992 | Potter | ............................ 600/431 |
| 5,647,368 A | 7/1997 | Zeng et al. | |
| 5,697,885 A | 12/1997 | Konomura et al. | |
| 5,801,763 A * | 9/1998 | Suzuki | ............................ 348/77 |
| 6,122,042 A | 9/2000 | Wunderman et al. | |
| 6,631,286 B2 | 10/2003 | Pfeiffer et al. | |
| 6,915,154 B1 | 7/2005 | Docherty et al. | |
| 2002/0013531 A1 * | 1/2002 | Hayashi | ........................ 600/476 |
| 2002/0038074 A1 | 3/2002 | Hakamata | |
| 2002/0138008 A1 | 9/2002 | Tsujita et al. | |
| 2003/0120129 A1 | 6/2003 | Nakamura | |
| 2003/0187319 A1 | 10/2003 | Kaneko et al. | |

(Continued)

FOREIGN PATENT DOCUMENTS

DE   198 04 797   8/1999

(Continued)

*Primary Examiner* — Tse Chen
*Assistant Examiner* — Joel F Brutus
(74) *Attorney, Agent, or Firm* — Drinker Biddle & Reath LLP (57) ABSTRACT

A sentinel lymph node detecting apparatus 1 according to an embodiment of the present invention includes: a light source unit 2, illuminating an excitation light 10 and an illumination light 11 onto a biological observation location 20 that includes a sentinel lymph node 21 near a tumor, into which a fluorescent dye that emits fluorescence is injected; an optical filter 3, transmitting a fluorescence image 11 and a normal image 13; an image pickup device 5, disposed integral to the light source unit 2 and picking up the fluorescence image 11 and the normal image 13 transmitted through the optical filter 3; and an image display device 7, displaying the observation images that have been picked up. The wavelength of the illumination light 11 is set to a value close to the wavelength of the fluorescence emitted from the fluorescent dye.

3 Claims, 6 Drawing Sheets

U.S. PATENT DOCUMENTS

2004/0109231 A1 6/2004 Haisch et al.

FOREIGN PATENT DOCUMENTS

| | | |
|---|---|---|
| JP | 9-154812 | 6/1997 |
| JP | 2810715 | 7/1998 |
| JP | 11-332820 | 12/1999 |
| JP | 2000-292353 | 10/2000 |
| JP | 2000-300509 | 10/2000 |
| JP | 2000-354583 | 12/2000 |
| JP | 2001-78205 | 3/2001 |
| JP | 2001-212070 | 8/2001 |
| JP | 2001-299676 | 10/2001 |
| JP | 2002-95663 | 4/2002 |
| JP | 2002-291682 | 10/2002 |
| JP | 2002-336196 | 11/2002 |
| JP | 2003-66145 | 3/2003 |
| JP | 2003-79570 | 3/2003 |
| JP | 2003-190103 | 7/2003 |
| JP | 2003-215469 | 7/2003 |
| JP | 2004-89236 | 3/2004 |
| JP | 2004-305382 | 11/2004 |
| WO | WO 01/22870 | 4/2001 |
| WO | WO 01/97902 | 12/2001 |
| WO | WO 03/077741 | 9/2003 |
| WO | WO 2004/006816 | 1/2004 |

* cited by examiner

LYMPH NODE DETECTOR

TECHNICAL FIELD

The present invention relates to a lymph node detecting apparatus for detecting a sentinel lymph node or other lymph node by use of a fluorescence image generated by a fluorescent dye.

BACKGROUND ART

A sentinel lymph node is a lymph node that is first reached by cancer cells from a tumor via lymph flow and is the lymph node with the highest possibility of metastasis by the cancer cells. Thus, if the sentinel lymph node is identified correctly and if metastasis by cancer cells is not found therein, it can be considered that there is no metastasis to other organs. Significant reductions in physical and psychological burdens placed on a patient, restraining of treatment costs by omission of ablative surgery, etc., are thus anticipated.

As methods of detecting the sentinel lymph node, dye methods and RI (radioisotope) methods are mainly known. With a dye method, for example, a blue dye, such as indigo carmine, is injected close to a tumor, the lymphatic duct that is dyed in blue is traced visually, and the lymph node that is reached first is detected as the sentinel lymph node. With an RI method, for example, a radioisotope that serves as a tracer is injected close to a tumor, a biological observation location that is presumed to include the lymph node, at which the radioisotope first arrives and accumulates, is probed from above the skin by a gamma probe, and the biological observation location at which gamma rays are detected is detected as the sentinel lymph node.

Methods of identifying a sentinel lymph node using a fluorescent dye have also been proposed. With the sentinel lymph node detecting apparatus disclosed in Japanese Published Unexamined Patent Application No. 2001-299676 (Document 1), a fluorescent dye is injected close to a tumor in advance, and light of a predetermined wavelength is illuminated as an excitation light onto a biological observation location, which lies in the periphery of the tumor that is presumed to include the sentinel lymph node. By then converting and displaying a near-infrared band fluorescence image, generated from the biological observation location, as a visible image, the sentinel lymph node is identified.

Fluorescence measurement methods are also described in Japanese Published Unexamined Patent Application No. H11-332820 (Document 2) and Japanese Published Unexamined Patent Application No. 2000-292353 (Document 3).

DISCLOSURE OF THE INVENTION

However, with the above-described conventional dye method, abundant experience is required to visually trace the lymphatic duct that is dyed in blue, and once the position of the sentinel lymph node is lost track of, the dyeing must be repeated.

With the above-described conventional RI method, although the above-described experience for visually tracing a lymphatic duct and repeating of dyeing are not required, there are such issues as the danger of exposing the surroundings to radiation due to use of a radionuclide, the high cost of the radioisotopes, etc.

With the above-described sentinel lymph node detecting apparatus of Document 1 that uses a fluorescent dye, although there is no danger of exposure to radiation, illumination light, made up of visible light, is used to obtain a normal image, and thus a filter for transmitting the visible light is required in addition to a filter for transmitting the fluorescence. An optical means for superimposing the image due to fluorescence and the image due to visible light is furthermore required, thus making the arrangement complicated and difficult to handle in medical situations.

Meanwhile, although acquisition of an image by a light source other than an excitation light source is described in Documents 2 and 3, this image is simply used as data for correction of a fluorescence observation image.

The present invention has been made to resolve the above issues, and an object thereof is to provide a lymph node detecting apparatus that is simple in apparatus arrangement and enables the position of a lymph node to be detected readily.

In order to achieve the above object, the present invention provides a lymph node detecting apparatus that includes: an excitation light source, illuminating an excitation light onto a biological observation location that includes a lymph node near a tumor, into which a fluorescent dye that emits a fluorescence of a predetermined wavelength has been injected in advance; an optical filter, transmitting light in a transmission wavelength band that includes the wavelength of the fluorescence emitted from the biological observation location upon illumination of the excitation light; an illumination light source, illuminating the biological observation location with an illumination light of a wavelength set so as to be included in the transmission wavelength band; an image pickup means, picking up a fluorescence image and a normal image, the fluorescence image resulting from the fluorescence emitted from the biological observation location and transmitted through the optical filter, the normal image resulting from reflected light due to reflection of the illumination light by the biological observation location and transmitted through the optical filter, the image pickup means outputting a respectively corresponding fluorescence observation image and normal observation image; and an image display means, displaying the fluorescence observation image and the normal observation image, output from the image pickup means, as images for detecting the lymph node. The wavelength of a lower limit of the above-described transmission wavelength band is preferably longer than the wavelength of the excitation light.

The above-described lymph node detecting apparatus has an arrangement enabling both the fluorescence observation image and the normal observation image to be displayed. The fluorescence observation image and the normal observation image can thus be compared to readily detect the position of a lymph node within a biological observation location. The optical filter transmits light in the transmission wavelength band that includes the wavelength of the fluorescence emitted from the biological observation location. Furthermore, the illumination light is set so that the wavelength thereof is included in the transmission wavelength band. Thus, both the fluorescence image due to the fluorescence emitted from the biological observation location and the normal image resulting from reflected light due to reflection of the illumination light by the biological observation location can be transmitted by a single optical filer. Because two different optical filters do not have to be used to transmit the fluorescence image and the normal image, an optical means for superimposing the fluorescence image and the normal image is not required. The arrangement is thus made simple, and a compact, simple, and inexpensive apparatus is made possible. The wavelength of the illumination light is set, as mentioned above, to be within the transmission wavelength band of the optical filter. Thus, in comparison to a case of using white light, blurring due to aberrations that occur during image pickup is suppressed. Such a detecting apparatus is especially useful for detecting the above-described sentinel lymph node.

Here, the illumination light source preferably illuminates the biological observation location with illumination light of a wavelength set to be close to the wavelength of the fluorescence. An optical filter of narrow transmission wavelength band can thus be used and the obtaining of the optical filter is thereby facilitated.

Preferably, the detecting apparatus furthermore has a supporting member that supports the excitation light source and the illumination light source integrally, and the supporting member is disposed integral to the image pickup means. By providing an arrangement in which the excitation light source, the illumination light source, and the image pickup means are integral, an apparatus of simple apparatus arrangement and easy handling can be realized.

In this case, the excitation light source and the illumination light source are preferably installed in a predetermined positional relationship on the same surface of the supporting member. Control of illumination of the excitation light and the illumination light onto a predetermined range of the biological observation location is thereby facilitated.

Preferably, the supporting member has a first principal surface, which supports the excitation light source and the illumination light source, and a surface defining a hole that passes through in a direction intersecting the first principal surface, and the optical filter is disposed inside the hole. With this arrangement, the excitation light source, the illumination light source, and the optical filter can be positioned readily, and an apparatus of simple apparatus arrangement and easy handling can be realized.

Preferably, the supporting member is a plate-like member and has a second principal surface that opposes the first principal surface, and the image pickup means is supported on the second principal surface so as to oppose the hole. With this arrangement, the positioning of the image pickup means with respect to the optical filter is also facilitated.

The lymph node detecting apparatus according to the present invention may have a plurality of the excitation light sources and a plurality of the illumination light sources. Preferably a plurality of columns, each formed by disposing a plurality of the excitation light sources and a plurality of the illumination light sources alternatingly in a predetermined direction, the columns aligned at predetermined intervals in the direction perpendicular to the predetermined direction and lying along the first principal surface. With this arrangement, the excitation light and the illumination light can be illuminated more uniformly onto the predetermined range of the biological observation location.

Preferably, of the excitation light sources and the illumination light sources, the direction of emission of each of excitation light sources and illumination light sources that are disposed in a periphery of the hole is inclined toward a central axial line of the hole. With this arrangement, the excitation light and the illumination light can be illuminated even more uniformly onto the predetermined range of the biological observation location.

The image display means is preferably enabled to be fit onto a head portion of an observer. The need to hold the lymph node detecting apparatus with a hand during observation is thereby eliminated, and the degree of freedom of work besides observation can be increased.

BEST MODES FOR CARRYING OUT THE INVENTION

A lymph node detecting apparatus according to a favorable embodiment of the present invention shall now be described in detail along with the drawings. In the description of the drawings, elements that are the same are provided with the same symbol and redundant description shall be omitted. The dimensional proportions in the drawings do not necessarily match those of the description.

Figure 1:
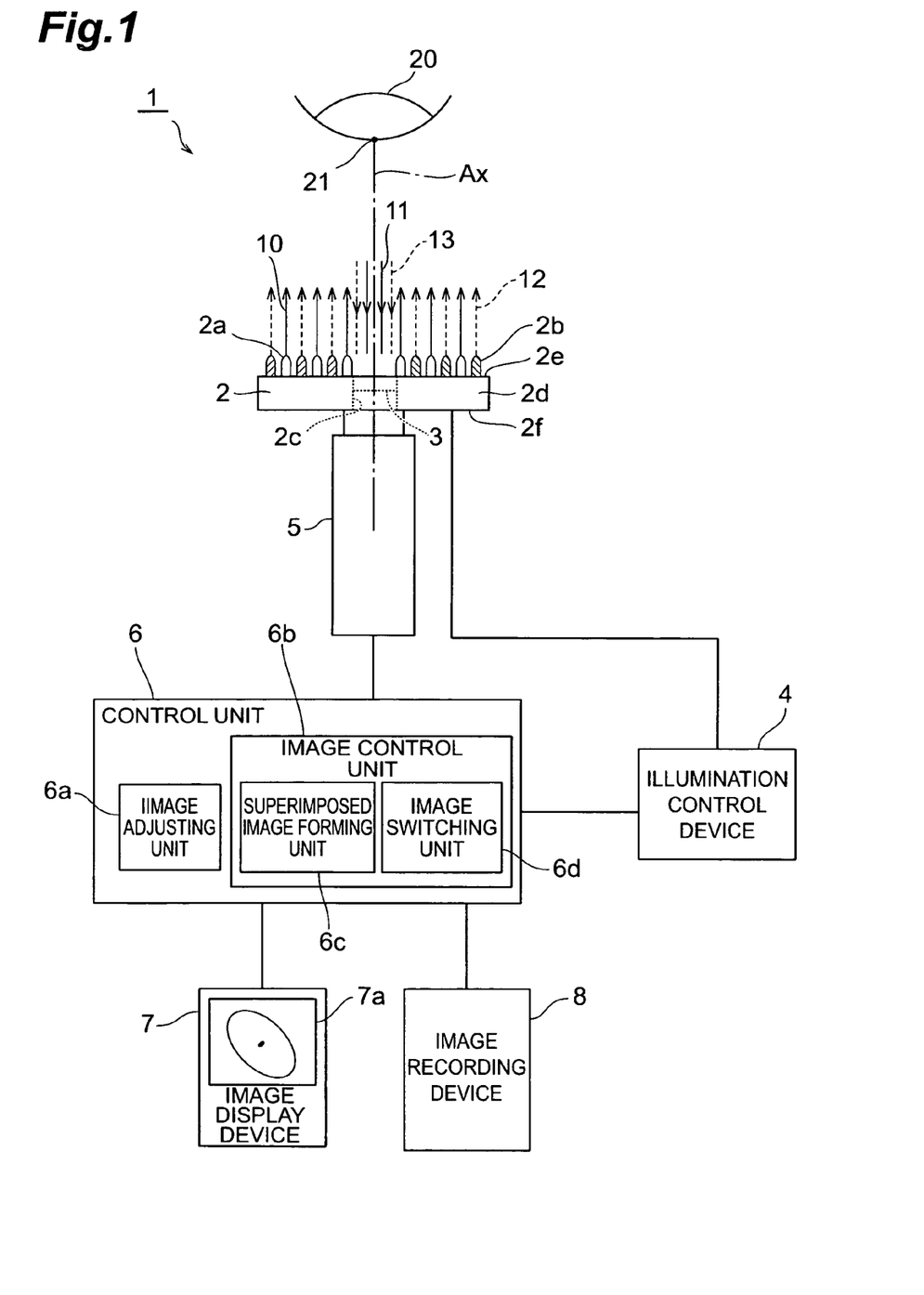
FIG. 1 is an arrangement diagram of a first embodiment of a sentinel lymph node detecting apparatus.
Figure 2:
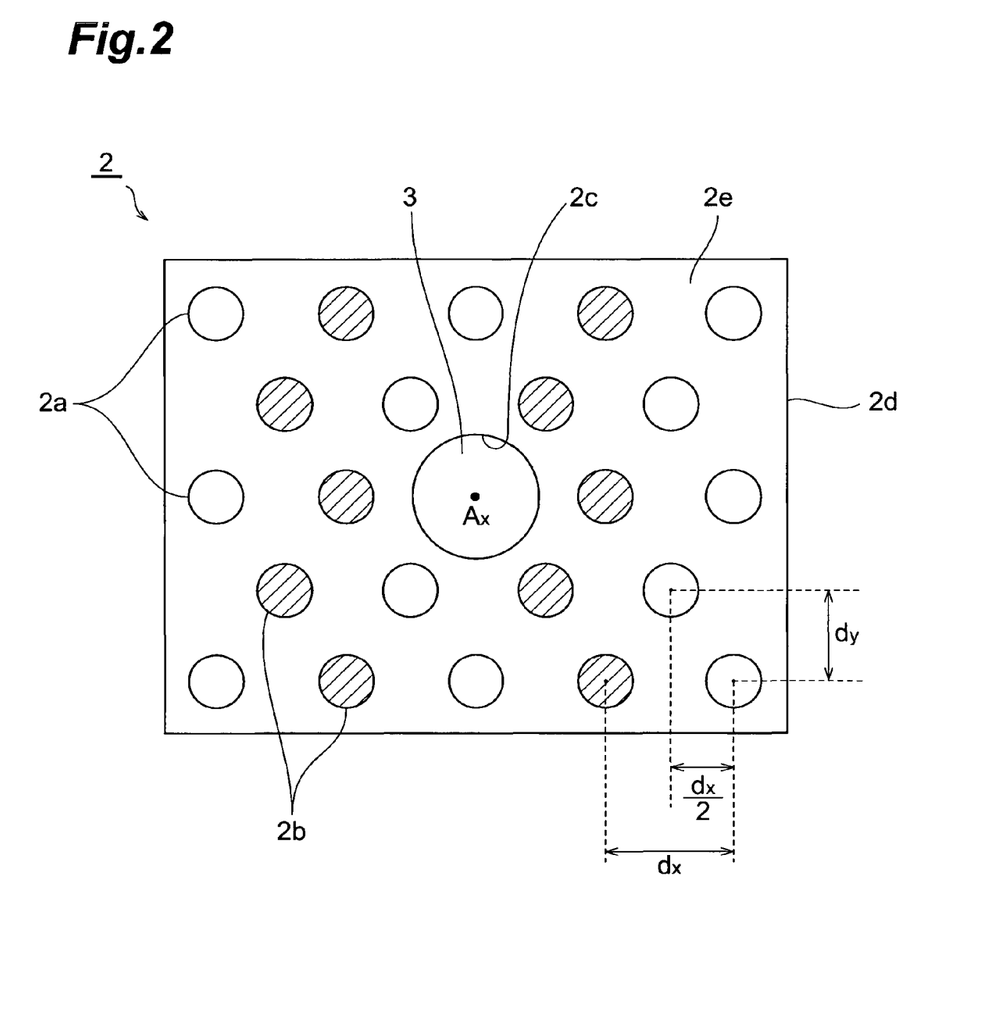
FIG. 2 is a front view of an arrangement of a light source unit used in the detecting apparatus shown in FIG. 1.

FIG. 1 is an arrangement diagram of a first embodiment of a sentinel lymph node detecting apparatus, which is a lymph node detecting apparatus according to the present invention. FIG. 2 is a front view of an arrangement of a light source unit used in the detecting apparatus shown in FIG. 1. The arrangement of the sentinel lymph node detecting apparatus according to the embodiment shall now be described with reference to FIG. 1 and FIG. 2. For the ease of viewing, illumination light sources are shaded in FIG. 1 and FIG. 2. In regard to light rays, excitation light and fluorescence, emitted from a fluorescent dye, are indicated by solid lines, and illumination light and reflected light, due to reflection of the illumination light by a biological observation location, are indicated by broken lines.

With this sentinel lymph node detecting apparatus 1, a sentinel lymph node 21 is detected from the biological observation location 20, located inside a human body or other living body and including the sentinel lymph node 21, by observation of an image (fluorescence image 11) due to the fluorescence emitted from the fluorescence dye in the biological observation location 20 and an image (normal image 13) due to reflected light resulting from reflection of the illumination light 12 by the biological observation location 20.

In the detection of the sentinel lymph node using this detecting apparatus 1, a fluorescent dye is injected close to a tumor inside the biological observation location 20 in advance. The fluorescence from the fluorescent dye that accumulates in the sentinel lymph node 21 is then observed to detect the lymph node.

The fluorescent dye used is selected suitably in consideration of the specific arrangement of the detecting apparatus 1, etc., and as an example of such a fluorescent dye, indocyanine green can be cited.

The detecting apparatus 1, shown in FIG. 1, includes a light source unit 2, an optical filter 3, an illumination control device 4, an image pickup device 5, a control unit 6, an image display device 7, and an image recording device 8.

The light source unit 2 has a plurality of excitation light sources 2a, a plurality of illumination light sources 2b, and a supporting plate 2d. Each of the excitation light sources 2a is arranged as a light source that emits, as the excitation light 10, light of the same wavelength, and is used to illuminate the excitation light 10 onto the biological observation location 20 that includes the sentinel lymph node 21.

Meanwhile, each of the illumination light source 2b is arranged as a light source that emits, as the illumination light 12, light of the same wavelength, and is used to illuminate the illumination light 12 onto the biological observation location 20 that includes the sentinel lymph node 21.

As the excitation light sources 2a and the illumination light sources 2b, laser diodes (LDs) or light emitting diodes (LEDs) are preferably used. The wavelength of the excitation light 10 supplied from the excitation light sources 2a is selected, based on the light absorbing characteristics, etc., of the fluorescent dye used for observation, from among wavelengths that can excite the fluorescent dye.

In regard to the wavelength of the illumination light 12, supplied from the illumination light sources 2b, a wavelength, which is set so as to be included in a transmission wavelength band of the optical filter 3 to be described below and is preferably a wavelength close to the wavelength of the fluorescence emitted from the fluorescent dye used for observation, is selected.

As shown in FIG. 2, the supporting plate 2d is a supporting member that integrally supports the excitation light sources 2a and the illumination light sources 2b. An optical axis Ax of the light source unit 2 is matched with a central axis of optical plate 2d. The supporting plate 2d has an opening portion 2c at a central position that includes the axis Ax, which is the optical axis and the central axis. This opening portion 2c is formed from a surface that defines a penetrating hole that is formed along the axial line Ax.

The excitation light sources 2a and the illumination light sources 2b are arrayed in two dimensions so as to surround the opening portion 2c on a front surface 2e, that is, a first principal surface of the supporting plate 2d. Specifically, as shown in FIG. 2, a plurality of one-dimensional arrays are respectively formed by aligning the excitation light sources 2a and the illumination light sources 2b alternately on the front surface 2e at fixed array intervals $d_x$ in a direction parallel to one side of the supporting plate 2d of rectangular form. These one-dimensional arrays are aligned at fixed array intervals $d_y$ in a direction perpendicular to the one-dimensional arrays while being shifted with respect to each other by just $d_x/2$ in the one-dimensional array direction, thereby forming a two-dimensional array. The light sources are not installed at the opening portion 2c. The front surface 2e is a surface perpendicular to the central axis Ax of the light source unit 2 and is the surface that is the front surface with respect to a biological observation location 20, which is the object of illumination by the excitation light 10 and the illumination light 12.

The opening portion 2c is for allowing the fluorescence image 11 and the normal image 13, which are made incident from the front of the light source unit 2, to pass through toward the rear. The fluorescence image 11 refers to the image resulting from the fluorescence emitted from the biological observation location 20 excited by illumination of the excitation light 10 of predetermined wavelength onto the biological observation location 20. The normal image 13 refers to the image resulting from the reflected light due to reflection of the illumination light 12 by the biological observation location 20.

Figure 6:
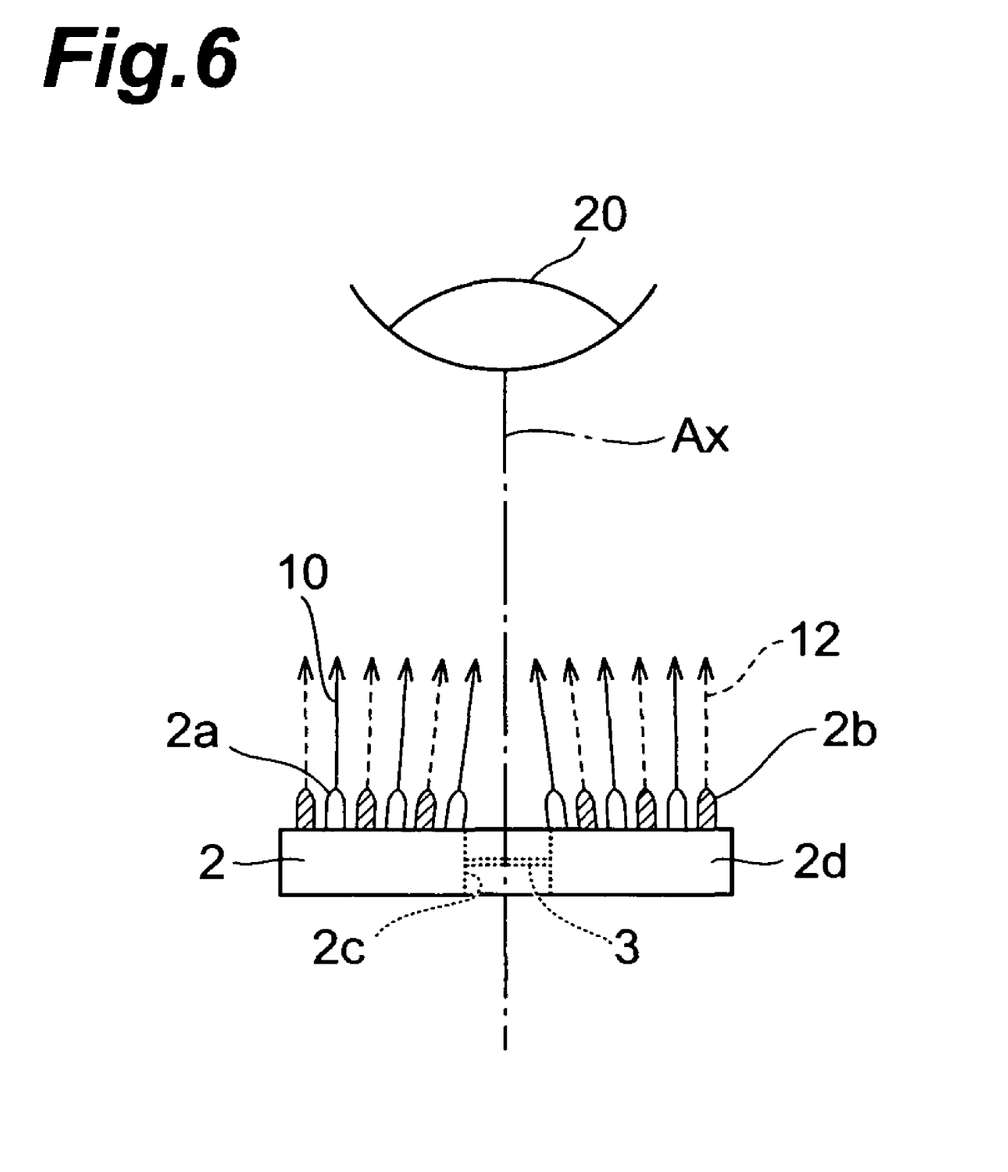
FIG. 6 is a plan view of another arrangement of a light source unit used in the detecting apparatus shown in FIG. 1.

FIG. 6 is a plan view of another arrangement of a light source unit used in the detecting apparatus shown in FIG. 1. With this arrangement, in order to prevent the weakening of the intensity distribution of the excitation light 10 and the illumination light 12, illuminated onto the biological observation location 20, due to the influence of the opening portion 2c, the excitation light sources 2a and the illumination light sources 2b near the opening portion 2c are favorably set so that the optical axes thereof are inclined toward the central axis Ax.

Figure 3:
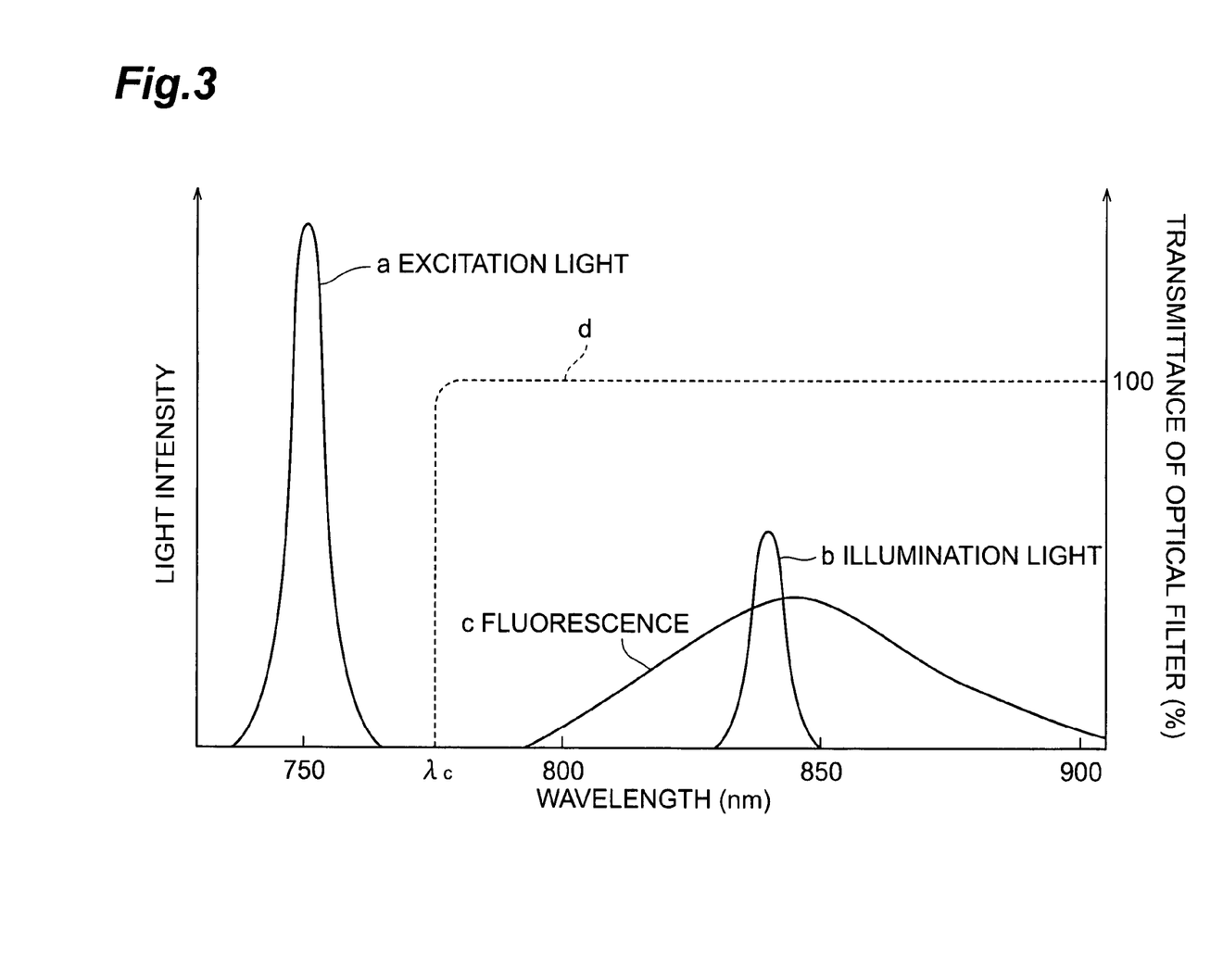
FIG. 3 is a graph of transmittance of an optical filter with respect to wavelength of light.

Inside the opening portion 2c of the supporting plate 2d is installed the optical filter 3. The optical filter 3 cuts the reflected light of the excitation light 10 and transmits light in a transmission wavelength band that includes the wavelength of the fluorescence emitted from the biological observation location 20. FIG. 3 is a graph of transmittance of the optical filter 3 with respect to wavelength of light in a case where indocyanine green is used as the fluorescent dye. An abscissa axis of the graph indicates the wavelength (nm) of light, an ordinate axis at one side indicates the transmittance of the optical filter 3 with respect to wavelength, and an ordinate axis at the other side indicates the intensity of light. Solid line curves a, b, and c in FIG. 3 indicate wavelength bands and intensity distributions of the different types of light, with a indicating the characteristics of the excitation light 10, b indicating the characteristics of the illumination light 12, and c indicating the characteristics of the fluorescence 11. A dotted line d in FIG. 3 indicates the transmittance of the optical filter 3 with respect to the wavelength of light. As shown in FIG. 3, the optical filter 3 cuts the excitation light 10 and transmits the illumination light 12 and the fluorescence 11.

Here as mentioned above, the wavelength of the excitation light 10 is selected from among wavelengths by which the fluorescent dye can be excited. Thus, when indocyanine green is used as the fluorescent dye, because the light absorption band thereof lies in the near-infrared wavelength band, a wavelength in the near-infrared wavelength band (for example, a wavelength of 750 nm) is selected appropriately and used as the excitation light 10 as indicated by the curve a in FIG. 3. In this case, the peak fluorescence wavelength of the fluorescent emitted from the biological observation location 20 is 845 nm as indicated by c in FIG. 3.

Also, the transmission wavelength band of the optical filter 3 is selected so as to cut the excitation light 10 and include the wavelength of the fluorescence emitted from the biological observation location 20. In the example shown in FIG. 3, the transmission wavelength band of the optical filter 3 is, as indicated by the curve d, a wavelength band, that has a wavelength $\lambda_c$, which is a longer wavelength than the wavelength of 750 nm of the excitation light 10 and is a shorter wavelength than the wavelength band of the fluorescence, as a lower limit value and transmits light at the longer wavelength side (including the wavelength $\lambda_c$) of this lower limit. Light in the transmission wavelength band is transmitted at a transmittance of 100%.

Furthermore, as the wavelength of the illumination light 12, a wavelength, which is set so as to be included in the transmittance wavelength band of the optical filter 3 and is preferably close to the wavelength of the fluorescence emitted from the fluorescent dye used for observation, is selected. Thus, in this case, light of a wavelength of 840 nm is selected as the illumination light as indicated by the curve b in FIG. 3.

As the optical filter 3, preferably an optical filter with a transmission wavelength band having not just a lower limit value but also an upper limit value is used. The optical filter 3 is also preferably installed at a front or internal portion of a lens of the image pickup device 5.

The illumination control device 4 is connected to the light source unit 2 and controls the illumination of the excitation light 10 and the illumination light 12 by the excitation light sources 2a and the illumination light sources 2b. For control of the illumination of the excitation light 10 and the illumination light 12, for example, the timing of illumination of light, the illumination time, or the intensity of the emitted light is controlled.

The image pickup device 5 is installed to the rear of the light source unit 2. In the present embodiment, the image pickup device 5 is disposed integral to the supporting plate 2d of the light source unit 2 with the optical axis Ax being matched. For example, the image pickup device 5 is supported by a rear surface 2f (second principal surface) opposite the front surface 2e so as to face the hole defined by the opening portion 2e. The fluorescence image 11 and the normal image 13 thus reach the image pickup device 5 upon passing through the opening portion 2c of the supporting plate 2d and being transmitted through the optical filter 3. The image pickup device 5 picks up the incident fluorescence image 11 and normal image 13 and outputs respectively corresponding fluorescence and normal observation images as image data.

As the image pickup device 5, for example, a CCD camera that can acquire a two-dimensional image is used. In particular, an image pickup device that can pick up light of the wavelength band of the fluorescence image 11 (a near-infrared wavelength band, since normally, a fluorescence observation image of approximately 800 nm is the object of detection) at high sensitivity is preferably used as the image pickup device 5. To the excitation light sources 2a, the illumination light sources 2b, and the image pickup device 5, a light source power supply and an image pickup device power supply are respectively connected as necessary. However, the power supplies, etc., are omitted from illustration in FIG. 1. As these devices, those that are battery-driven may be used.

The control unit 6 is provided for the fluorescence observation image and the normal observation image output from the image pickup device 5. The control unit 6 performs, as necessary, adjustment or switching of the fluorescence observation image or the normal observation image or superimposition of these observation images. For transmission of the image data from the image pickup device 5 to the control unit 6, a wired or a wireless transmission method may be used.

The control unit 6 has an image adjusting unit 6a and an image control unit 6b. The image adjusting unit 6a is used to perform automatic or manual adjustment of the luminance and contrast of the fluorescence observation image or the normal observation image output from the image pickup device 5.

The image control unit 6b is an arrangement in the detecting apparatus 1 that enables display of the fluorescence observation image or the normal observation image in a switching manner and display of these images simultaneously in a superimposed manner. The image control unit 6b thus has a superimposed image forming unit 6c and an image switching unit 6d. For switching display, the image switching unit 6d switches the displayed observation image automatically or according to manual operation. The superimposed image forming unit 6c superimposes the fluorescence observation image and the normal observation image output from the image pickup device 5 and forms a superimposed observation image.

The control unit 6 is also connected to the illumination control device 4.

The image display device 7 and the image recording device 8 are connected to the control unit 6. On a display unit 7a of the image display device 7, image data of the observation image output from the control unit 6 are displayed in the form of an observation image for detecting the sentinel lymph node 21. As this image display device 7, for example, a CRT monitor, a liquid crystal display mounted to the CCD camera that is the image pickup device 5, etc., may be used. The image recording device 8 is a recording means for recording the image data output from the control unit 6. As this image recording device 8, for example, a videotape recorder that records the image data onto a videotape that is a recording medium may be used.

A method for detecting a sentinel lymph node using the sentinel lymph node detecting apparatus 1 shown in FIG. 1 shall now be described. First, the fluorescent dye, indocyanine green, is injected close to a tumor. After the elapse of a predetermined time, the indocyanine green reaches the sentinel lymph node 21 due to lymph flow.

Then, to acquire the fluorescence observation image, the excitation light 10 of 750 nm wavelength is illuminated by the excitation light sources 2a onto the biological observation location 20 that includes the sentinel lymph node 21. The fluorescence image 11 of the near-infrared wavelength band is thereby generated from the biological observation location 20. The fluorescence image 11 is subsequently transmitted through the optical filter 3 and picked up by the CCD camera that is the image pickup device 5. The fluorescence observation image that is picked up is output to the control unit 6 and after being adjusted, etc., there as necessary, is displayed on the display unit 7a of the image display device 7.

Meanwhile to acquire the normal observation image, the illumination light 12 of 840 nm wavelength is illuminated by the illumination light sources 2b onto the biological observation location 20 that includes the sentinel lymph node 21. The normal image 13, resulting from the reflected light due to reflection of the illumination light 12 by the biological observation location 20, is thus obtained. The wavelength of the illumination light 12 is preferably set close to the wavelength of the fluorescence emitted from indocyanine green so as to be within the transmission wavelength band of the optical filter 3. The normal image 13 is subsequently transmitted through the optical filter 3 and picked up by the CCD camera that is the image pickup device 5. The normal observation image that is picked up is output to the control unit 6 and after being adjusted, etc., there as necessary, is displayed on the display unit 7a of the image display device 7.

To acquire a superimposed observation image, first, the fluorescence observation image and the normal observation image are acquired at the control unit 6 by the methods described above. Then, in the superimposed image forming unit 6c, the images are superimposed to form the superimposed observation image. The superimposed observation image that is formed is output to the image display device 7 and displayed on the display unit 7a of the image display device 7.

The display of these observation images is controlled by the image control unit 6b of the control unit 6 so that each observation image can be displayed in a switching manner or be displayed simultaneously in a superimposed manner as the superimposed observation image. As a method, besides the superimposed observation image, of superimposingly displaying the fluorescence observation image and the normal observation image simultaneously, there is, for example, a method of displaying the normal observation image as a black-and-white image on the display unit 7a of the image display device 7 in advance, and then superimposingly displaying the fluorescence observation image that is colored. The fluorescence observation image and the normal observation image can be displayed simultaneously by this method as well.

The control unit 6 is also connected to the illumination control device 4. The illumination control device 4 controls, for example by means of a mechanical switch or an electrical switch, the illumination of the excitation light sources 2a and the illumination light sources 2b according to the observation image to be displayed. The illumination can thereby be controlled in various ways and, for example, to display the fluorescence observation image and the normal observation image alternately, the excitation light sources 2a and the illumination light sources 2b may be made to illuminate alternately. The image data of the observation image output from the control unit 6 are recorded as necessary in the recording medium in the image recording device 8.

Based on the observation images thus displayed, the position of the lymph node expressed in the fluorescence observation image is marked on skin by a pen, etc. Thereafter, the measurement is stopped, and the marked portion of the skin is incised to perform biopsy of the lymph node.

Effects of the sentinel lymph node detecting apparatus 1 according to the above-described embodiment shall now be described.

With the above-described embodiment, both the fluorescence observation image and the normal observation image can be acquired. Switching display is enabled by switching the observation image to be displayed by means of the image switching unit 6d of the control unit 6. Simultaneous, superimposed display is enabled by the forming of the superimposed observation image at the superimposed image forming unit 6c of the control unit 6 or by superimposition of the observation images by means of the image switching unit 6d.

Figure 4:
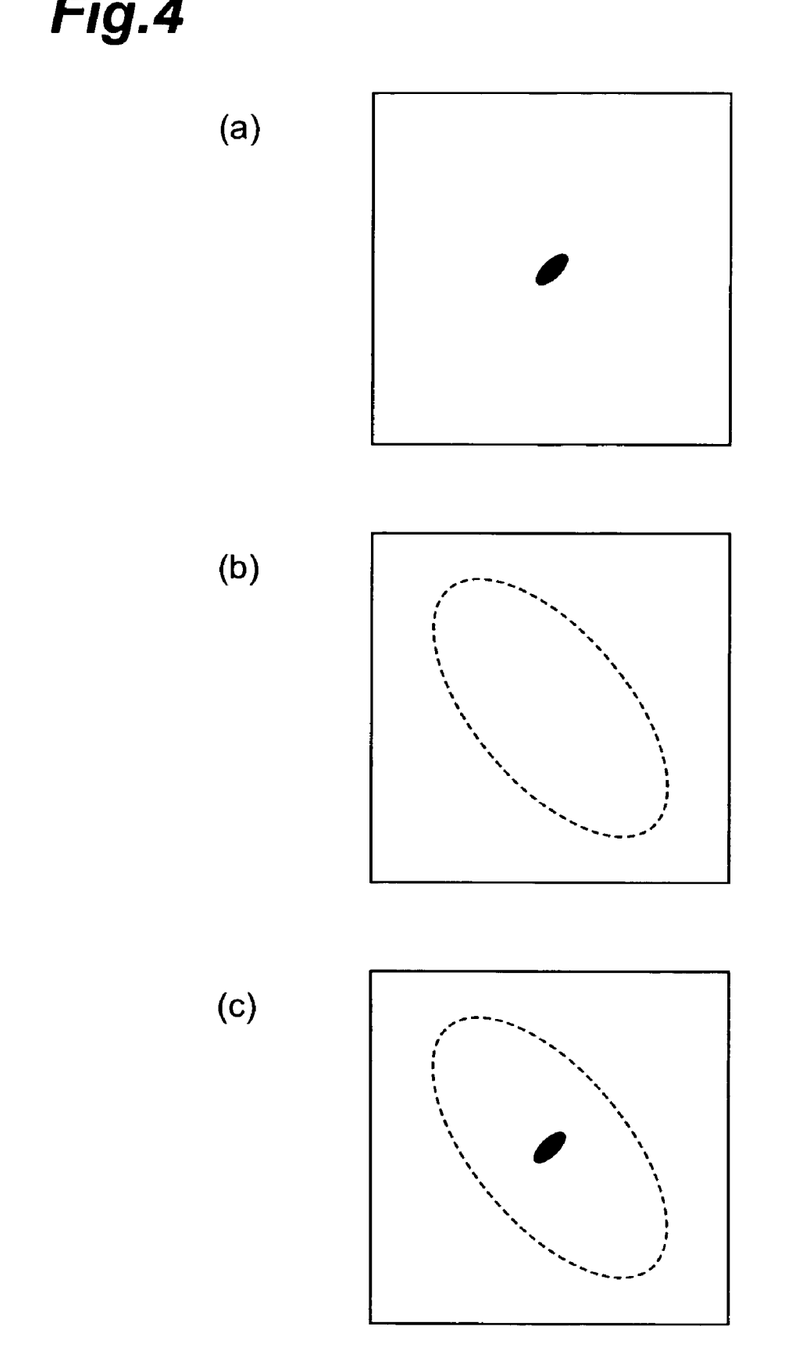
FIG. 4 shows a schematic diagram of a fluorescence observation image (a), a normal observation image (b), and a superimposed observation image (c) regarding a biologist observation location.

In FIG. 4 are schematically shown a fluorescence observation image (a), a normal observation image (b), and a superimposed observation image (c) that are displayed at the image display device 7. By thus enabling switching display, comparison of the fluorescence observation image and the normal observation image is enabled. By enabling superimposed display, from which portion of the biological observation location 20 the fluorescence is being emitted can be confirmed clearly. Because the desired observation image can thus be displayed according to purpose, the position of the lymph node within the biological observation location 20 can be detected readily.

The optical filter 3 cuts the light due to reflection of the excitation light 10 by the biological observation portion 20 and transmits light in the transmission wavelength band that includes the wavelength of the fluorescence 11 emitted from the biological observation location 20. The illumination light 12 is also set so that its wavelength is included in the transmission wavelength band. Thus, both the fluorescence image 11 and the normal image 13 can be transmitted with a single optical filter 3 and there is no need to prepare separate optical filters for acquiring the fluorescence image 11 or the normal image 13. The arrangement of the detecting apparatus 1 can thus be made simple.

Also, as described above, two different optical filters do not have to be used to transmit the fluorescence image 11 and the normal image 13. A half mirror or other optical means or an image device, etc., for superimposing the fluorescence image 11 and the normal image 13 is thus not required. The arrangement can thus be made even simpler. By the arrangement being simplified thus, a simple, inexpensive, and compact apparatus is made possible.

The wavelength of the illumination light 12 is set so as to be within the transmission wavelength band of the optical filter 3. Thus, in comparison to using white light as the illumination light, blurring due to lens aberrations that occur in the image pickup process is suppressed. In particular, when light of a wavelength in the near-infrared wavelength band is used as the excitation light, most of the light included in white light cannot be transmitted through the optical filter that cuts the excitation light. It is thus difficult to acquire a normal image using white light as the illumination light without exchange of the optical filter.

Also, by light of a wavelength near the fluorescence wavelength being used as the illumination light 12, even when an optical filter of narrow transmission wavelength band is used, the wavelength of the illumination light 12 falls within the transmission wavelength band of the optical filter. Because the optical filter is thus not required to have a wide transmission wavelength band, the obtaining of the optical filter is facilitated. Also, by use of an optical filter, having just the fluorescence wavelength band that includes the wavelength of the illumination light as the transmission wavelength band, more of the unnecessary light can be cut.

With the arrangement of the detecting apparatus 1, shown in FIG. 1, the supporting plate 2d, on which the excitation light sources 2a and the illumination light sources 2b are installed, and the image pickup device 5, which picks up the fluorescence image 11 and the normal image 13, are disposed integrally. Because, matching of the optical axes of the light source unit 2 and the image pickup device 5 and other installation adjustment work are thus made unnecessary, image pickup of the fluorescence image 11 and the normal image 13 can be performed efficiently at the image pickup device 5. Also, there is no need to move the light source unit 2 and the image pickup device 5 separately in moving the detecting apparatus 1, and the apparatus can be made compact. The detecting apparatus 1 of simple apparatus arrangement and easy handling is thus realized.

Furthermore, the excitation light sources 2a and the illumination light sources 2b are installed at a predetermined positional relationship on the same surface 2e of the supporting plate 2d. Alternating illumination of the excitation light 10 and the illumination light 12 onto the biological observation location 20 can thus be performed readily. Also, the excitation light 10 and the illumination light 12 can be illuminated simultaneously if necessary.

Figure 5:
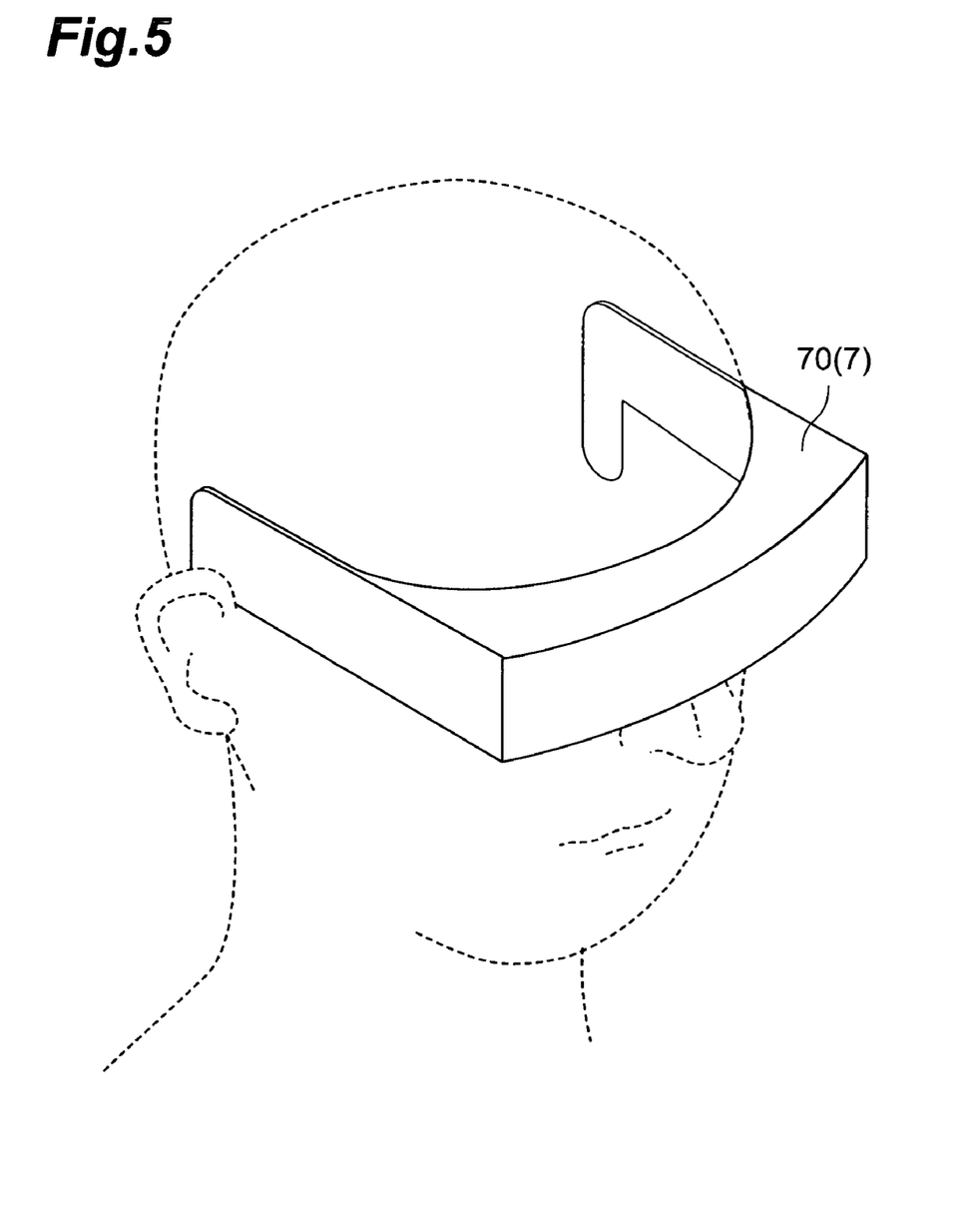
FIG. 5 is a perspective view of a manner in which the detecting apparatus shown in FIG. 1 is fit onto a head portion of an observer.

The control unit 6, the image display device 7, and the image recording device 8 may be set up as separate or integral components with respect to the light source unit 2 and the image pickup device 5. As the image display device 7, an arrangement (such as a goggle type or glasses type arrangement) that can be fitted onto a head portion of the observer as in the case of an image display device 70 shown in FIG. 7 is preferably used. The need to move or hold image display device 7, etc., with a hand during observation is thereby eliminated and the degree of freedom of work besides observation can be increased. In this case, the excitation light sources, the illumination light sources, the image pickup device, the control unit, the illumination control unit, and other components besides image display device 7 may be arranged to be integrally fitted along with the image display device.

Also, with the present embodiment, the image recording device 8 is provided for the observation image from the control unit 6. The observation image during observation can thereby be recorded. However, such an image recording device 8 does not have to be provided if it is unnecessary.

An image is acquired using a light source that emits light of a wavelength near a fluorescence wavelength in the arrangement of Document 2 and using a light source that emits light of a wavelength that does not excite a fluorescent substance in the arrangement of Document 3 to apply image processing to the image data acquired from a fluorescence image. However, these images are used simply as data for correction of the fluorescence observation image. The fluorescence observation image and the normal observation image thus cannot be observed simultaneously. In contrast, the present invention enables the fluorescence observation image and the normal observation image to be observed simultaneously and is thus useful for detecting the position of a sentinel lymph node.

The sentinel lymph node detecting apparatus according to the present invention is not restricted to the above-described embodiment and arrangement example, and various modifications are possible. For example, although in regard to the excitation light source and the illumination light source, the light source unit 2, having the excitation light sources 2a and the illumination light sources 2b, is used, a single excitation light source and a single illumination light source may be used instead. Also, in place of using separate light sources as the excitation light source and the illumination light source, a dual wavelength LED that emits light of two wavelengths may be used. In this case, the lights of the two different wavelengths that are emitted from the dual wavelength LED are used as the excitation light and the illumination light, respectively. In regard to the image data output from the image pickup device, if noise in the image data is a problem in the case of a live moving image (30 Hz), etc., a recursive filter or other filtering method may be employed to reduce the noise and obtain a clearer fluorescence image.

Also, although in the embodiment described above, the excitation light sources 2a and the illumination light sources 2b are installed on the supporting plate 2d, an arrangement, which does not have such a supporting member and in which the light sources are not installed on a single supporting member, is also possible. Also, although in the embodiment described above, the supporting plate 2d is used as the supporting member, the supporting member is not restricted to a plate light structure. Also, although in the embodiment described above, the excitation light sources 2a and the illumination light sources 2b are installed on the same flat surface of the supporting plate 2d, the installation of the light sources is not restricted to that on the same flat surface of the supporting plate. The positional relationship of the light sources on the supporting plate is also not restricted to the array relationship of the above-described embodiment. Also, the control unit 6 does not have to be provided with the image adjusting unit 6a, the superimposed image forming unit 6c, or the image switching unit 6d if any of these is unnecessary. A structure without the illumination control device 4 and the control unit 6 is also possible if these are unnecessary.

The detecting apparatus of the above arrangement is not restricted to a sentinel lymph node detecting apparatus and can be applied generally as a lymph node detecting apparatus.

In regard to the fluorescent dye used to observe the sentinel lymph node, although a water-soluble fluorescent dye is generally used, because a fluorescent dye, with which a fluorescent dye is dissolved in physiological saline, etc., is generally small in molecular weight, it may not stay in the lymph node that is reached first and may reach a second or a third lymph node. In this case, by using a quantum dot of a diameter of several dozen nm that emits near-infrared fluorescence or a fluorescent tracer, in which a fluorescent reagent is bound to a metal colloid or to latex beads, improvement of the precision of identification of the sentinel lymph node position can be anticipated.

INDUSTRIAL APPLICABILITY

The present invention can be used as a lymph node detecting apparatus that is simple in apparatus arrangement and enables the position of a lymph node to be detected readily.

The invention claimed is:

1. A lymph node detecting apparatus comprising:
an excitation light source, illuminating an excitation light onto a biological observation location that includes a lymph node near a tumor into which a fluorescent dye that emits a fluorescence of a predetermined wavelength has been injected in advance;
an optical filter, transmitting light in a transmission wavelength band that includes the wavelength of the fluorescence emitted from the biological observation location upon illumination of the excitation light;
an illumination light source, illuminating the biological observation location with an illumination light of a wavelength set so as to be included in the transmission wavelength band, the illumination light being a near-infrared light;
a single image pickup device, picking up a fluorescence image and a normal image, the fluorescence image resulting from the fluorescence emitted from the biological observation location and transmitted through the optical filter, the normal image resulting from reflected light due to reflection of the illumination light by the biological observation location and transmitted through the optical filter, the image pickup means outputting a respectively corresponding fluorescence observation image and normal observation image; and
an image display means, displaying the fluorescence observation image and the normal observation image, output from the image pickup means, as images for detecting the lymph node,
wherein the illumination light source illuminates the observation object with the illumination light of a wavelength that is set close to the wavelength of the fluorescence,
wherein the wavelength of a lower limit of the transmission wavelength band is longer than the wavelength of the excitation light and wherein the lymph node detecting apparatus having a plurality of the excitation light sources and a plurality of the illumination light sources, and a plurality of columns, each formed by disposing the excitation light sources and the illumination light sources in a first direction, the columns aligned at predetermined intervals in a second direction perpendicular to the first direction.

2. A lymph node detecting apparatus comprising:
an excitation light source, illuminating an excitation light onto a biological observation location that includes a lymph node near a tumor into which a fluorescent dye that emits a fluorescence of a predetermined wavelength has been injected in advance;
an optical filter, transmitting light in a transmission wavelength band that includes the wavelength of the fluorescence emitted from the biological observation location upon illumination of the excitation light;
an illumination light source, illuminating the biological observation location with an illumination light of a wavelength set so as to be included in the transmission wavelength band, the illumination light being a near-infrared light;
a single image pickup device, picking up a fluorescence image and a normal image, the fluorescence image resulting from the fluorescence emitted from the biological observation location and transmitted through the optical filter, the normal image resulting from reflected light due to reflection of the illumination light by the biological observation location and transmitted through the optical filter, the image pickup means outputting a respectively corresponding fluorescence observation image and normal observation image; and an image display means, displaying the fluorescence observation image and the normal observation image, output from the image pickup means, as images for detecting the lymph node, wherein the illumination light source illuminates the observation object with the illumination light of a wavelength that is set close to the wavelength of the fluorescence, the lymph node detecting apparatus further comprising: a supporting member that supports the excitation light source and the illumination light source integrally, and the supporting member is disposed integral to the image pickup means, wherein the excitation light source and the illumination light source are installed in a predetermined positional relationship on the same surface of the supporting member, wherein the supporting member has a first principal surface, supporting the excitation light source and the illumination light source, and a surface defining a hole that passes through in a direction intersecting the first principal surface, and the optical filter is disposed inside the hole the lymph node detecting apparatus having a plurality of the excitation light sources and a plurality of the illumination light sources, and a plurality of columns, each formed by disposing the excitation light sources and the illumination light sources alternatingly in a first direction, the columns aligned at predetermined intervals in a second direction perpendicular to the first direction.

3. The lymph node detecting apparatus according to claim 2, wherein of the excitation light sources and the illumination light sources, the direction of emission of each of excitation light sources and illumination light sources that are disposed in a periphery of the hole is inclined toward a central axial line of the hole.

* * * * *